(12) United States Patent
Garcia et al.

(10) Patent No.: US 11,559,491 B2
(45) Date of Patent: Jan. 24, 2023

(54) ORAL COMPOSITIONS AND THE PREPARATION METHODS THEREOF

(71) Applicant: CEVA SANTE ANIMALE, Libourne (FR)

(72) Inventors: Rosita Garcia, Change (FR); Romain Charles, Meslay du Main (FR)

(73) Assignee: CEVA SANTE ANIMALE, Libourne (FR)

( * ) Notice: Subject to any disclaimer, the term of this patent is extended or adjusted under 35 U.S.C. 154(b) by 0 days.

(21) Appl. No.: 16/638,372

(22) PCT Filed: Aug. 17, 2018

(86) PCT No.: PCT/EP2018/072297
§ 371 (c)(1),
(2) Date: Feb. 11, 2020

(87) PCT Pub. No.: WO2019/034763
PCT Pub. Date: Feb. 21, 2019

(65) Prior Publication Data
US 2020/0360290 A1 Nov. 19, 2020

(30) Foreign Application Priority Data
Aug. 17, 2017 (EP) .................................... 17306078

(51) Int. Cl.
*A61K 9/20* (2006.01)
*A61K 9/16* (2006.01)
(Continued)

(52) U.S. Cl.
CPC .......... *A61K 9/2095* (2013.01); *A61K 9/0056* (2013.01); *A61K 9/1617* (2013.01);
(Continued)

(58) Field of Classification Search
CPC .................................................... A61K 9/2095
See application file for complete search history.

(56) References Cited

U.S. PATENT DOCUMENTS

| 4,321,263 A | * | 3/1982 | Powell | H01B 3/441 424/738 |
| 5,637,313 A | * | 6/1997 | Chau | A61K 31/52 424/440 |

(Continued)

FOREIGN PATENT DOCUMENTS

| JP | 2005-538128 A | 12/2005 |
| JP | 2011-528702 A | 11/2011 |

(Continued)

OTHER PUBLICATIONS

Herbert A. Lieberman, Leon Lachman, and Joseph B. Schwartz. "Pharmaceutical Dosage Forms: Tablets." vol. 1, Second Edition. ISBN 0-8247-8044-2, pp. i-xviii and 1-592, originally published 1989, Marcel Dekker Inc. New York. (Year: 1989).*

(Continued)

*Primary Examiner* — Isaac Shomer
(74) *Attorney, Agent, or Firm* — Leason Ellis LLP (57) ABSTRACT

The present invention relates to a process for preparing a solid composition comprising at least one active ingredient and at least one excipient comprising: i) mixing said at least one active ingredient and said at least one excipient in a granulator to obtain wet granules; ii) spreading wet granules on a tray and let stand for 2 to 24 hours between 15 and 25° C.; iii) compressing granules obtained after step ii) with a tablet press; and iv) collecting the solid composition. The invention further relates a solid composition obtained by such process.

16 Claims, 1 Drawing Sheet

(51) Int. Cl.
  *A61K 9/00*      (2006.01)
  *A61K 31/365*    (2006.01)
  *A61K 31/4985*   (2006.01)
  *A61K 47/10*     (2017.01)
  *A61K 47/12*     (2006.01)
  *A61K 47/38*     (2006.01)
  *A61K 47/44*     (2017.01)

(52) U.S. Cl.
  CPC .......... *A61K 9/1682* (2013.01); *A61K 31/365* (2013.01); *A61K 31/4985* (2013.01); *A61K 47/10* (2013.01); *A61K 47/12* (2013.01); *A61K 47/38* (2013.01); *A61K 47/44* (2013.01)

(56) References Cited

U.S. PATENT DOCUMENTS

| | | | |
|---|---|---|---|
| 2003/0228368 | A1 | 12/2003 | Wynn et al. |
| 2008/0160067 | A1* | 7/2008 | Boeckh ................ A61K 9/0056 424/441 |
| 2011/0189244 | A1 | 8/2011 | Derrieu et al. |
| 2014/0343004 | A1 | 11/2014 | Derrieu et al. |

FOREIGN PATENT DOCUMENTS

| | | |
|---|---|---|
| JP | 2013-536821 A | 9/2013 |
| JP | 2014-532041 A | 12/2014 |
| WO | 96/18387 A1 | 6/1996 |
| WO | 2004/014346 A1 | 2/2004 |
| WO | 2005/013714 | 2/2005 |
| WO | 2008/134819 | 12/2008 |
| WO | 2009/000843 | 12/2008 |
| WO | 2009/064859 | 5/2009 |
| WO | 2012/031934 A1 | 3/2012 |
| WO | 2012/049156 | 4/2012 |
| WO | WO-2012049156 A1 * | 4/2012 ........... A61K 9/2018 |
| WO | 2013/037650 | 3/2013 |
| WO | 2013/119442 | 8/2013 |
| WO | 2014/079825 | 5/2014 |
| WO | WO-2017106812 A1 * | 6/2017 ........... A61K 9/2013 |

OTHER PUBLICATIONS

Pawan Jalwal, Jyoti Dahiya, Balvinder Singh, Renu. "Formulation and Evaluation of Chewable Tablets of Loratadine by Wet Granulation Method." The Pharma Innovation Journal 2015; 4(5): 106-108. (Year: 2015).*

Nuria Jimenez, et al., "Stability Improvement of a Liquid Enzyme Product", AAPS Pharmscitech, 2009, vol. 10, No. 4, pp. 1313-1320.

S Mujumdar, "Drying: Principles and Practice International Workshop on drying of Food and Biomaterials", Jun. 7, 2011, Retrieved from the Internet: URL: http://www.kmutt.ac.th/dtri/pdf/Drying Principles and Practice.pdf [retrieved on Dec. 14, 2017].

International Search Report and Written Opinion in PCT/EP2018/072297 dated Oct. 19, 2018.

* cited by examiner

ORAL COMPOSITIONS AND THE PREPARATION METHODS THEREOF

FIELD OF THE INVENTION

The present invention relates to the veterinary field. More particularly, the invention concerns the preparation of compositions for therapeutic purposes, which are formulated in solid form to be administered to animals, more particularly to improve oral administration and to guarantee treatment compliance.

BACKGROUND OF THE INVENTION

Oral route is currently the priority route for administering medications by health professionals or owners to animals and typically to domestic animals. Indeed, the parenteral route (intramuscular, sub-cutaneous, intradermal, and intravenous) has a number of drawbacks. This parenteral route may cause hematomas and abscesses for the animal and often requires a specialist. Such parenteral route for administering medication is thus not pleasant for the animal and quite constraining for the owner.

However, pharmaceutical or nutraceutical compositions administered by oral route are not always well accepted by the animal and it is well known that acceptation is based on main properties of such compositions, for instance palatability, texture, shape, and size. In addition to these parameters, it is crucial to fully control the quantity of the active ingredient(s) in the composition and, preferably, prepare such compositions with a lowest cost.

It exists a large number of commercially available oral formulations. Such formulations are for instance tablets, pills, hard capsules, soft capsules, chewable gums or soft chews, and pellets. However, it has chiefly been ascertained that treatment via oral route with solid formulations is not always properly followed on account of the difficulty in administering a full treatment in animals, reducing thereby its compliance. Indeed, the oral administration of solid compositions to animals is often difficult on account of the bad taste of some active ingredients and excipients and the much developed sense of smell and taste in animals. It has thus been observed in animals that the main reason which makes it difficult even impossible to properly follow oral treatment is the lack of palatability of the solid composition.

The palatability of a solid composition administered by oral route corresponds to the acceptance and voluntary ingestion thereof by an animal. The palatability depends on different characteristics of the solid composition. For instance, the taste is a crucial parameter for an improved palatability and a lot of flavors or palatable materials are added in the solid compositions. The texture of the solid composition characterized by hardness, brittleness, softness, elasticity, color have further to be considered. Also, the shape and the size of the solid composition may facilitate the acceptation of the solid composition by the animal.

In this context, soft chews have been developed and manufactured according to two major processes, which are a process with forming and a process with extrusion.

The process with forming comprises a first step of blending ingredients to form a soft dough, which is then molded in a specifically defined mold without compression or heat, using a forming machine such as machine type Formax F6. Such process is more particularly disclosed by the following applications: WO 2009/06485 and WO 2012/049156 in the name of Bayer, WO 2014/079825 in the name of Intervet and for which the dough is heated between 35 and 45° C., and WO 2013/119442 in the name of Merial. However, the process with forming requires a long step of maturation after demolding at room temperature or in a stove in order to harden the soft chew tablet so that they can be more easily handled and packaged.

The process with extrusion requires a screw, wherein mixed ingredients are pushed through an orifice and cut to a specific size by blades. Such process also requires a control of pressure and temperature. This process is more particularly disclosed in the following applications WO 2005/013714 in the name of Novartis and WO 2008/134819 in the name of Jurox, for which the extrudate is cut into equal piece.

The processes with forming and with extrusion allow to manufacture soft chewable compositions in a unique shape and a unique size only. Indeed, it is required to define a shot size in the process with extrusion, which is not always very accurate, and a specific mold is required for the process with forming. In addition, the soft chewable compositions obtained by such processes have to be hardened thanks to a long maturation step but still stay friable when they are handled and packed. Another drawback is that the active ingredient(s) is not homogenously dispersed, which is not suitable for a good compliance of the treatment.

Friulchem SPA has developed a process for preparing soft chews. This process is disclosed by the international application WO 2013/037650 and provides the soft chew "FC-CUBES". The process of Friulchem SPA comprises a step of mixing dry and liquid components followed by a granulation step by vaporizing animal or vegetable fats. Granules are then directly calibrated and compressed with a special stock cube press to give the soft chew "FC-CUBES", which are rather palatable thanks to high proportion of palatable ingredients used including fats and flavors. However, the "FC-CUBES" must be administrated in whole into the animal since it cannot be bi- or quadrisected depending on the weight of the animal because of the high proportion of fat ingredients. Also, the process of Friulchem SPA allows to obtain a soft chew in a unique shape according to the press used.

In view of the above, there is still a need to develop new processes for the manufacture of solid compositions intended to be administered by an oral route in an animal while guarantying and improving treatment compliance.

SUMMARY OF THE INVENTION

In this context, the inventors have surprisingly implemented a process for preparing a solid composition allowing to obtain a new oral dosage form improving the treatment compliance. Such process, particularly comprising a step of spreading of wet granules at room temperature, provides a solid composition in an intermediate form between usual tablets and soft chewable formulations, and can be named "soft tablet". The term "soft tablet" as disclosed herein thus refers to a solid composition obtained by the process of the invention using a tablet press.

The solid composition or "soft tablet" prepared by the process as disclosed herein is suitable for any active ingredients to be orally administered in an animal and exhibit major advantages compared to the classic soft chew and tablet formulations. More particularly, the "soft tablet" comprises at least one active ingredient, which is more homogenously dispersed compared to the active ingredient(s) comprised in the classic soft chewable formulations. The "soft tablet" is also not sticky and is easier to handle and package than the soft chew. The "soft tablet" can further be bi- or quadrisected, as classic tablet forms. It has also the advantage of being manufactured in many possible shapes thanks to the use of classic tablet press. Production costs are also significantly reduced when compared to processes of the prior art since the process according to the present invention is as fast as for conventional tablet production. Therefore, the process as disclosed herein does not necessitate an elaborate and costly equipment, and provides "soft tablets" having both the advantages of classic soft chew and tablet formulations.

The present invention therefore relates to a process for preparing a solid composition comprising at least one active ingredient, and at least one excipient, wherein the process comprises the following successive steps:
 i) mixing said at least one active ingredient and said at least one excipient in a granulator to obtain wet granules;
 ii) spreading the obtained wet granules on a tray and let stand for 2 to 24 hours between 15 and 25° C.;
 iii) compressing granules obtained after step ii) with a tablet press; and
 iv) collecting the solid composition.

In a first embodiment, said solid composition comprises at least one active ingredient chosen from among anti-infectives such as antibiotics and sulfonamides, cardiotonics, internal and external anti-parasitics, insecticides, insect growth inhibitors, anti-arthritics, anti-inflammatories whether or not steroidal, anti-histaminics, hormones such as prostaglandins, substances for digestive therapy such as gastro-intestinal dressings and sedatives, anti-ulcer agents and substitution flora, anti-diarrhoeals, hepato-protectors, antispasmodics, laxatives, intestinal antiseptics, substances for respiratory therapy such as respiratory analeptics, antitussives, bronchodilators, bronchial and mucolytic fluidifiers and respiratory antiseptics, substances acting on the nervous system such as analgesics, sedatives and tranquillizers, anti-epileptics, anaesthetics, orexigenics, anorexigenics, substances for immunity therapy such as interleukins and interferon, substances for anticancer therapy such as antimitotics and cytostatics, macro-, micro-nutrients and trace elements, vitamins, plant extracts, extracts from animal organs, and a mixture thereof.

In a second embodiment, said solid composition comprises at least one active ingredient chosen from among an active nutraceutical or a food supplement ingredient, preferably chosen from among plant extracts, animal extracts, substitution flora, macro-, micro-nutrients and trace-elements, and a mixture thereof.

In a particular embodiment, said solid composition comprises at least one excipient chosen from among a palatable material, a humectant, a binder, a lubricant, a filler, a disintegrant, and a mixture thereof.

In a preferred embodiment, said solid composition comprises:
 between 0.01 and 20.00%, preferably between 1.00 and 10% by weight of said at least one active ingredient,
 between 15.00 and 30.00%, preferably about 20.00% by weight of said at least one palatable material,
 between 15.00 and 35.00%, preferably between 20.00 and 30.00% by weight of said at least one humectant,
 between 20.00 and 40.00%, preferably about 24.50% by weight of said at least one binder,
 between 0.10 and 10.00%, preferably about 5.00% by weight of said at least one lubricant,
 between 10.00 and 30.00%, preferably between 15.00 and 25.00% by weight of said at least one filler, and
 between 0.10 and 10.00%, preferably about 4.00% by weight of said at least one disintegrant, relative to the total weight of the solid composition.

In a particular embodiment, said solid composition further comprises at least one preservative and/or at least one antioxidant, and/or at least one chelating agent.

In a preferred embodiment, the present invention relates to a process comprising the following successive steps:
 i) a) mixing said at least one active ingredient, said at least one palatable material, said at least one binder, said at least one filler, said at least one lubricant, and said at least one disintegrant in a granulator;
 i) b) spraying said at least one humectant onto the blend of step i) a) and mixing to obtain wet granules;
 ii) a) spreading the wet granules obtained after step i) b) and let stand for 2 to 24 hours between 15 and 25° C.;
 ii) b) milling the granules obtained after step ii) a) with an oscillating granulator, and then sifted, through a 800 to 2000 μm sieve, preferably through a 1250 μm sieve;
 ii) c) optionally letting stand the granules for 2 to 24 hours at room temperature;
 iii) a) optionally blending the granules obtained after step ii) b) or step ii) c) with at least one disintegrant and/or at least one filler in a blender.
 iii) b) blending the granules obtained after step ii) b), ii) c) or iii) a) with at least one lubricant in a blender;
 iii) c) compressing the blend obtained after step iii) b) with a tablet press; and
 iv) collecting the solid composition.

Another objet of the invention is a solid composition obtained by the process as disclosed herein.

DETAILED DESCRIPTION OF THE INVENTION

Figure 1:
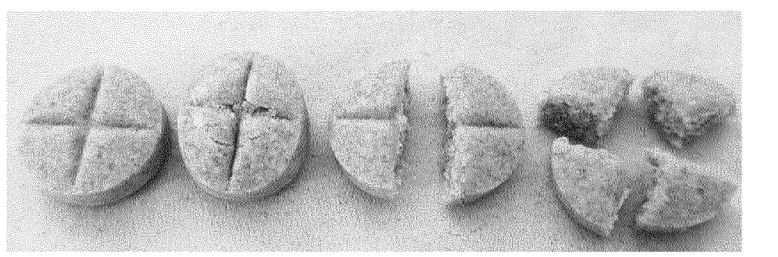
FIG. 1: Picture of a quadrisected "soft tablet" obtained by the process of the invention.

The present invention herein provides a process for preparing a solid composition comprising at least one active ingredient, and at least one excipient, wherein the process comprises the following successive steps:
 i) mixing said at least one active ingredient and said at least one excipient in a granulator to obtain wet granules;
 ii) spreading wet granules on a tray and let stand for 2 to 24 hours between 15 and 25° C.;
 iii) compressing granules obtained after step ii) with a tablet press; and
 iv) collecting the solid composition.

The present invention further provides a solid composition obtained by the process as disclosed herein.

Solid Composition

The solid composition obtained by the process according to the invention can be considered as an intermediate form between classic tablets and soft chews and corresponds to a "soft tablet".

Such "soft tablets" comprise at least one active ingredient homogenously dispersed and accurately dosed, and at least one excipient. By "active ingredient" is meant an ingredient of a medicinal product, a nutraceutical or food supplement having a therapeutic effect or a biological activity, or also a non-therapeutic effect.

Contrary to the classic soft chews, the "soft tablets" are not sticky, not friable and hard enough to be manipulated and packaged. Also, they can be bi- or quadrisected according to the type, the size, and the weight of the animal for which the "soft tablets" are orally administered, and can be in various shapes according to the mold used in the press tablet. For instance, the "soft tablets" can be in a circular, oval, cube, square, triangular, clover form, and any other form according to the mold used. Also, the "soft tablets" can be obtained in several sizes. In a circular form, the diameter of the "soft tablets" may vary between 5 and 30 mm, 5 and 25 mm, 5 and 20 mm, 5 and 15 mm, preferably between 10 and 15 mm. More preferably, the diameter of the "soft tablets" is about 14 mm. The own properties of the "soft tablets" according to the invention satisfy the requirements of the parameters for an improved observance of the treatment applied in an animal.

Contrary to the classic tablets, "soft tablets" hardness cannot be measured by classic equipment because of its softness. The conventional process to evaluate tablet hardness is compression testing whereby the analyst generally aligns the tablet in a repeatable way, and the tablet is squeezed by 2 jaws. A continuous force is applied with a spring and screw thread until the tablet starts to break. When the tablet fractures, the hardness is read with a sliding scale. However, in the case of the soft tablets according to the present invention, the soft tablet bends and the force is zero.

The solid compositions or "softs tablets" of the invention are suitable for any treatments orally administered to an animal and a skilled person can chose the quantity and the nature of the at least one active ingredient according to the biological effect he wishes to obtain.

For instance, the at least one active ingredient is chosen from among anti-infectives such as antibiotics and sulfonamides, cardiotonics, internal and external anti-parasitics, insecticides, insect growth inhibitors, anti-arthritics, anti-inflammatories whether or not steroidal, anti-histaminics, hormones such as prostaglandins, substances for digestive therapy such as gastro-intestinal dressings and sedatives, anti-ulcer agents and substitution flora, anti-diarrhoeals, hepato-protectors, antispasmodics, laxatives, intestinal antiseptics, substances for respiratory therapy such as respiratory analeptics, antitussives, bronchodilators, bronchial and mucolytic fluidifiers and respiratory antiseptics, substances acting on the nervous system such as analgesics, sedatives and tranquillizers, anti-epileptics, anaesthetics, orexigenics, anorexigenics, substances for immunity therapy such as interleukins and interferon, substances for anticancer therapy such as antimitotics and cytostatics, macro-, micro-nutrients and trace elements, vitamins, plant extracts, extracts from animal organs, and a mixture thereof.

Preferably, the at least one active ingredient is a substance having a repulsive odor and/or or taste. These are for example aldosterone antagonists, angiotensin conversion enzyme inhibitors, antagonists of the AT-1 receptor of angiotensin II, inotropic agents, inodilators, vasodilators, diuretics, digitalis drugs, beta blockers and/or calcium antagonists. The process is also advantageous when said pharmaceutical active substances are unstable and sensitive to moisture.

Among the aldosterone antagonists, spironolactone and eplerenone, or the metabolites of these compounds, which among others include canrenone, canrenoic acid, 1513-0H canrenone, 21-0H canrenone, potassium canrenone, 7α-thio-spironolactone, 7α-thiomethyl-spironolactoneor 6-β-hydroxy-7-α-thiomethyl spironolactone may be mentioned.

Among the angiotensin conversion enzyme inhibitors, alacepril, benazepril, captopril, cilazapril, delapril, enalapril, fosinopril, imidapril, idrapril, lisinopril, perindopril, quinapril, ramipril, saralasin acetate, termocapril, trandolapril, ceranapril, moexipril, spirapril and their pharmaceutically acceptable derivatives of these compounds such as in particular the salts and esters may be mentioned.

Among the inodilators, pimobendane or levosimendane may be mentioned.

In a preferred embodiment, the at least one active ingredient is spironolactone and/or benazepril and/or enalapril.

The solid compositions as disclosed herein are particularly useful for treating non-human animals suffering from cardiac insufficiency such as congenital cardiopathy or acquired cardiopathy as described in particular in the international publication WO 2009/000843. Also, an object of the present invention is a solid veterinary composition as disclosed herein, for use thereof in the treatment and/or the prevention of cardiac insufficiency in non-human animals.

A further object of the present invention is a method for treating and/or preventing cardiac insufficiency in a non-human animal, comprising administering a solid veterinary composition as disclosed herein in a non-human animal.

A further object of the present invention is a use of a solid veterinary composition as disclosed herein for the manufacture of a drug for treating and/or preventing cardiac insufficiency in a non-human animal.

Thus, the solid veterinary composition according to the present invention can, for example, comprises a therapeutically effective daily dose of an aldosterone receptor antagonist such as spironolactone and/or derivatives or metabolites thereof of between about 0.88 and 5.00 mg/kg/day (preferably about 2.00 mg/kg/day) and a dose of an angiotensin conversion enzyme inhibitor, such as benazepril, of between 0.10 to 0.60 mg/kg/day (preferably about 0.25 mg/kg/day).

Other active ingredients are for example compounds having antiparasitic activity against endoparasites and/or ectoparasites. These include without limitation the macrocyclic lactones: avermectins and milbemycins such as preferably ivermectin, eprinomectin, selamectin, moxidectin and milbemycin oxime, benzimidazoles, imidazothiazoles, tetrahydropyrimidines, organophosphates, piperazines, antimicrobial agents or also antibiotic agents such as preferably amoxicillin.

Other active ingredients may be selected from organosulfur compounds such as omeprazole, aiming to reduce the acid secretions of the stomach.

In a further preferred embodiment, the solid veterinary composition according to the present invention comprises milbemycin, milbemycin oxyme, both milbemycin oxyme and praziquantel, praziquantel, lufenuron, ivermectin, both ivermectin and pyrantel, lufenuron, levamizole, doxycycline or a dog appeasing pheromone.

The "softs tablets" of the invention are further suitable for any oral treatments intended to improve the welfare of the animal. In this context, the "soft tablet" comprises at least one active ingredient chosen from among an active nutraceutical and a food supplement ingredient. Particularly, the active nutraceutical or the food supplement ingredient is chosen from among extracts for their anti-arthritic action such as chondroitin sulfate, chitosan and its derivatives S-Adenosyl Methionine (SAMe), for their anti-ulcer and/or anti-stress action such as fermented soy extract, for their insecticidal or insect repellent action such as pyrethrums, vitamins such a vitamin C, vitamin D3, substitution flora such as *Enterococcus faecium*, micro-nutrients such as selenium provided by a strain of *Saccharomyces cerevisiae*, for their appeasing effect such as appeasing pheromones e.g.: Adaptil. Preferably, the active nutraceutical or the food supplement ingredient is chosen from among plant extracts, animal extracts, substitution flora, macro-, micro-nutrients and trace-elements, and a mixture thereof.

The solid compositions or "soft tablets" of the invention further comprise at least one excipient and, notably, a mixture of particular excipients providing the desired properties of the "soft tablets". The at least one excipient can be chosen from among a palatable material, a humectant, a binder, a lubricant, a filler, a disintegrant, and a mixture thereof.

The palatable material provides a taste and an odor for the soft tablet, which is thus more accepted by the animal and thereby improving the compliance. The palatable material can be sweet and/or can derived from meat ingredients, or any natural, natural identical or artificial flavoring substances. It also comprises flavors such as essential oils, terpene derivatives (menthol), franeol, test enhancers such as sodium glutamate, sweeteners such as aspartame, sodium saccharin, maltol, polyols such as sorbitol, isomalt, maltitol, mannitol, and lactitol. In a preferred embodiment, the "soft tablet" comprises without limitation at least one palatable chosen from among meat, meat powders, fish powders, cheese powders, milk derivatives, liver powder, the extracts of these animal substances or their derivatives, yeasts, yeast extracts such as beer yeast, vegetable fibers, vegetable products and by-products such as malt extracts, fenugreek, apple, carrot, fodder beet, sugar beet, thyme, alfalfa, sugar cane, cereals such as oats, wheat, rice, corn, soy, their derivatives such as flours and a mixture thereof, crystallized sugar, powder sugar glucose, invert sugar, molasses, caramel, honey and its derivatives, sodium chloride, and a mixture thereof. In a preferred embodiment, the palatable material is a pig liver powder, a chicken liver flavor, a chicken flavor, yeast extract, malt extract, and a mixture thereof.

The humectant, the binder, the lubricant, the filler, and the disintegrant provides the specific physical properties of the "soft tablets" such as a hardening suitable for a good breakability, a friability suitable for a good handling and packaging, and a soft aspect for being manufactured in a non-limited shape number.

In a preferred embodiment, the humectant is chosen from among propylene glycol, glycerin, sorbitol, polyethylene glycol, and liquid oils such as soya bean oil, peanut oil, olive oil, groundnut oil, rapeseed oil, sunflower oil, palm oil, coconut oil, peanut oil, fish oil, and a mixture thereof.

In a further preferred embodiment, the binder is chosen from among polyvinyl alcohol polymers, polyvinylpyrrolidone, the copolymers of vinylpyrrolidone and vinyl acetate, maltodextrin, carboxymethylcellulose, its salts and derivatives, alginic aid and its salts, zein, pectins, arabic gum, acacia gum, tragacanth gum, karaya gum, xanthan gum, guar gum, carrageenans, gelatin, pullulan polymers, agar polymers, starches and their derivatives, carbomers, acrylic acid cross-linked with polyalkenyl ethers, polycarbophils, and a mixture thereof. In a more preferred embodiment, the binder is chosen from among maltodextrin, pregelatinized starch, xanthan gum, guar gum, and a mixture thereof.

In a further preferred embodiment, the lubricant is chosen from among polyethylene glycol, magnesium or calcium stearate, stearic acid, vegetable oil, hydrogenated glyceryl palmitostearate, sodium stearyl fumarate, and a mixture thereof, preferably polyethylene glycol 6000, magnesium stearate, stearic acid, and a mixture thereof.

In a further preferred embodiment, the filler is chosen from among maltodextrin, cyclodextrin, lactose, talc, silica, silicates, phosphates, cellulose, cellulose powder, microcrystalline cellulose, croscarmellose, mica, carbonates, sugar (polysaccharides), and a mixture thereof. In a more preferred embodiment, the filler is chosen from among cellulose, microcrystalline cellulose, lactose, sugar, and a mixture thereof.

In a further preferred embodiment, the disintegrant is croscarmellose, crosspovidone, starch, sodium starch glycolate and a mixture thereof.

The solid compositions or "soft tablets" of the invention may further comprise any other excipients such as those described above. For instance, the "soft tablets" may further comprise at least one preservative, at least one antioxidant, at least one chelating agent, at least one coloring agent, and/or at least one pH regulator.

In a preferred embodiment, the preservative is chosen from among parabens, benzoic acid, sodium benzoate, sorbic acid, potassium sorbate, and a mixture thereof.

In a further preferred embodiment, the antioxidant is chosen from among ascorbic acid, its salts and derivatives, sodium or potassium metabisulphite, sodium bisulphite, butylhydroxyanisole, butylhydroxytoluene, gallic acid and its derivatives such as propyl gallate, and a mixture thereof.

In a further preferred embodiment, the chelating agent is chosen from among EDTA and its salts, tartaric acid and its salts, and a mixture thereof.

In a further preferred embodiment, the at least one coloring agent is chosen from among iron oxides, titanium oxides, curcumin, caramel, carotenes, and a mixture thereof.

In a further preferred embodiment, the pH regulator is chosen from among citric acid, its salts and derivatives, sodium carbonates, delta glucono lactone, and a mixture thereof.

It will be understood that the excipients as described above may have several functions. For instance, polyethylene glycol may be both a humectant and a lubricant, sugar may be both a palatable material and a filler, croscarmellose may be both a filler and a disintegrant, etc.

In a more preferred embodiment, the "soft tablet" comprises milbemycin, milbemycin oxyme, both milbemycin oxyme and praziquantel, praziquantel, lufenuron, ivermectin, both ivermectin and pyrantel pamoate, lufenuron, levamizole, doxycycline or a dog appeasing pheromone, a palatable material chosen from among pig liver powder, chicken liver flavor, chicken flavor and yeasts, a humectant chosen from among propylene glycol, glycerin, sorbitol, polyethylene glycol, soya bean oil, and peanut oil, a binder chosen from among maltodextrin, pregelatinized starch, xanthan gum, and guar gum, a lubricant chosen from among polyethylene glycol 6000, magnesium stearate, and stearic acid, a filler chosen from among sugar, cellulose, and lactose, and a croscarmellose as disintegrant.

In a further more preferred embodiment, the solid composition or "soft tablet" comprises: between 0.01 and 20.00%, preferably between 1.00 and 10.00% by weight of said at least one active ingredient, between 15.00 and 30.00%, preferably about 20.00% by weight of said at least one palatable material, between 15.00 and 35.00%, preferably between 20.00 and 30.00% by weight of said at least one humectant, between 20.00 and 40.00%, preferably about 24.50% by weight of said at least one binder, between 0.10 and 10.00%, preferably about 5.00% by weight of said at least one lubricant, between 10.00 and 30.00%, preferably between 15.00 to 25.00% by weight of said at least one filler, and between 0.10 and 10.00%, preferably about 4.0% by weight of said at least one disintegrant, relative to the total weight of the solid composition.

As used herein, the term "about" will be understood by a person of ordinary skill in the art and will vary to some extent on the context in which it is used. If there are uses of the term which are not clear to persons of ordinary skill in the art given the context in which it is used, "about" will mean up to plus or minus 20%, preferably 10% of the particular term.

As used herein, an "animal" comprises, without limitation, birds such as canaries, finches, lovebirds, caiques and cockatoos, and non-human mammal such as canidae, for instance dogs, foxes, coyotes, and wolfs, felidae, for instance cats, lions, and panthers, bovidae, for instance cattle and dairy cow, equidae, for instance horses, and camelidae, for instance camel. In a particular embodiment, the animal is a companion animal, preferably a dog or a cat, preferably a dog.

Process

The process for preparing a solid composition or a "soft tablet" as disclosed herein comprises i) a granulation step, ii) a let standing step of the granules, iii) a compression step, and iv) a collecting step. More particularly, the process comprises the following successive steps:
  i) mixing said at least one active ingredient and said at least one excipient in a granulator to obtain wet granules;
  ii) spreading the obtained wet granules on a tray and let stand for 2 to 24 hours between 15 and 25° C.;
  iii) compressing granules obtained after step ii) with a tablet press; and
  iv) collecting the solid composition.

In a preferred embodiment, the granulation step i) is performed in two times and comprises a first step i) a) in which the powder ingredients including said at least one active ingredient, said at least one palatable material, said at least one binder, said at least one filler, said at least one lubricant, said at least one disintegrant are first mixed in a granulator, and a second step i) b) in which said at least one humectant, including oil humectant are sprayed onto the blend of step i) a) and then mixed to obtain wet granules.

Optionally, the powder ingredients may be sieved prior the granulation step.

The at least one active ingredient may be added as a powder, as granulates or coated granulates, complexed with maltodextrin or cyclodextrin, or in a liquid form.

The let standing step ii) consisting to spread the wet granules on a tray and let stand or wait for 2 to 24 hours at room temperature, i.e. between 15 and 25° C., allows the liquids ingredients to be absorbed into the granules, thereby providing the specific physical properties of the "soft" tablets obtained by such process. The temperature should in any case not be greater than 25 to 30° C. in order to prevent generating a very sticky paste. The implementation of a process including steps i), iii), followed by a molding step i.e. without implementing step ii), will automatically provide classic soft chew, which are softer, more friable, and wherein the active ingredient is less accurately dispersed, compared to the "soft tablets" of the invention.

In the context of the present invention, the sense of the term "tray" is not limitative and include any device for which wet granules can be let stand at room temperature. For instance, wet granules can be let stand at room temperature on a bench, a table, a box, or a plate . . . .

In a preferred embodiment, the granules after let standing step ii) are milled with an oscillating granulator, and then sifted, preferably through a 800 to 2000 μm sieve, preferably a 1250 μm sieve (Step ii) b)). Optionally, the granules are then let stand for 2 to 24 hours at room temperature (Step ii) c)).

The compression step iii) is performed using a classic tablet press, i.e. with classic tooling, especially in the pharmaceutical or veterinary field. Indeed, the granules obtained after step ii) or step ii) b) or ii) c) are quite hardened and solid to be used in a press currently used for the manufacture of conventional tablets. Thus, the compression step does not require a specific machine to compress the granules, which is very important from a scale-up and economical process. The shape of the "soft tablets" of the invention depends on the mold used for the compression step and the breakability in a bi- or quadrisection depends on the punch used.

Optionally, the process comprises a step iii) a) of blending the granules with at least one disintegrant and/or at least one filler in a blender before the compression step. In a particular embodiment, the process further comprises a step iii) b) of blending the granules with at least one lubricant in a blender.

Therefore, a more preferred embodiment of the invention is a process comprising the following successive steps:
  i) a) mixing said at least one active ingredient, said at least one palatable material, said at least one binder, said at least one filler, said at least one lubricant, and said at least one disintegrant in a granulator;
  i) b) spraying said at least one humectant onto the blend of step i) a) and mixing to obtain wet granules;
  ii) a) spreading the wet granules obtained after step i) b) on a tray and let stand for 2 to 24 hours between 15 and 25° C.;
  ii) b) milling the granules obtained after step ii) a) with an oscillating granulator, and then sifted, preferably through a 800 to 2000 μm sieve, preferably through a 1250 μm sieve;
  ii) c) optionally let standing the granules for 2 to 24 hours at room temperature;
  iii) a) optionally blending the granules obtained after step ii) b) or step ii) c) with at least one disintegrant and/or at least one filler in a blender;
  iii) b) blending the granules obtained after step ii) b), ii) c) or iii) a) with at least one lubricant in a blender;
  iii) c) compressing the blend obtained after step iii) b) with a tablet press; and
  iv) collecting the solid composition.

Particularly, the granule obtained after let standing step ii), and optionally after milling step ii) b) with an oscillating granulator through a 800 to 2000 μm sieve, and optionally after let standing step ii) c) comprises:
  said at least one active ingredient in a range between 0.01 and 20.00%, preferably between 1.00 and 10.00% by weight,
  said at least one palatable material in a range between 15.00 and 30.00%, preferably about 20.00% by weight,
  said at least one humectant in a range between 15.00 and 35.00%, preferably between 20.00 and 35.00% by weight,
  said at least one binder in a range between 20.00 and 40.00%, preferably about 24.50% by weight,
  said at least one lubricant in a range between 0.01 and 10.00%, preferably between 0.10 and 5.00% by weight,
  said at least one filler in a range between 0.10 and 20.00%, and
  said at least one disintegrant in a range between 0.10 and 10.00%, preferably about 4.00% by weight,
  relative to the total weight of the granule.

Particularly, the solid composition or "soft tablet" comprises:
- said granule obtained after the let standing step ii), and optionally after the milling step ii) b) and ii) c), in a range between 83.50 and 99.98%, preferably about 90.75% by weight,
- said at least one filler, preferably cellulose, lactose, sugar, croscarmellose, and a mixture thereof in a range between 0.01 and 15.00%, preferably about 7.50% by weight, and
- said lubricant, preferably magnesium stearate, stearic acid, and a mixture thereof, in a range between 0.01 and 2.50%, preferably about 1.75% by weight, relative to the total weight of the solid composition.

More particularly, the solid composition or "soft tablet" comprises:
- between 0.01 and 20.00%, preferably between 1.00 and 10.00% by weight of said at least one active ingredient,
- between 15.00 and 30.00%, preferably about 20.00% by weight of said at least one palatable material,
- between 15.00 and 35.00%, preferably between 20.00 and 30.00% by weight of said at least one humectant,
- between 20.00 and 40.00%, preferably about 24.50% by weight of said at least one binder,
- between 0.10 and 10.00%, preferably about 5.00% by weight of said at least one lubricant,
- between 10.00 and 30.00%, preferably between 15.00 and 25.00% by weight of said at least one filler, and
- between 0.10 and 10.00%, preferably about 4.00% by weight of said at least one disintegrant, relative to the total weight of the solid composition.

Further aspects and advantages of the invention will be disclosed in the following experimental section. The examples below illustrate the present invention and are given as non-limiting illustrations.

EXAMPLES

Example 1: Process to Manufacture a Soft Tablet Comprising (Doxycycline)

In a granulator, all powder ingredients are mixed together in the amounts specified below:

| | |
|---|---|
| Doxycycline hyclate | 23.08 g |
| Yeast extract | 52.95 g |
| Chicken flavor | 12.46 g |
| Maltodextrin | 43.26 g |
| Pregelatinized starch | 37.37 g |
| Guar gum | 3.27 g |
| Xanthan gum | 1.40 g |
| Dextrose | 26.47 g |
| Microcrystalline cellulose | 17.13 g |
| Croscarmellose | 14.02 g |
| PEG 6000 | 6.23 g |

Then, humectants are sprayed onto the blend (sorbitol 30.21 g and glycerin 26.47 g premixed together) followed by the oily humectant soya oil (20.24 g). The resulting material is mixed to generate wet granules.

The wet granules are then spread on tray and left standing for 24 hours at a temperature of about 20° C.

The granules are then milled with an oscillating granulator through a 1250 µm sieve Granules were spread and left at ambient temperature for 6 hours.

The resulting granules were first blended in a blender with 17.27 g of microcrystalline cellulose, followed by addition of 6.80 g of stearic acid, and 1.36 g of magnesium stearate.

The granules were then compressed in a tablet press into tablets called soft tabs.

Tablets of 340 mg and 1530 mg were produced. 340 mg soft tablets containing 20 mg doxycycline were oblong with a punch size of 12.7 mm while 1530 mg soft tablets containing 90 mg doxycycline were round with a punch size of 16 mm.

The resulting tablet composition contains the following components:

| Ingredient | Product | WT % |
|---|---|---|
| Active ingredient | Doxycycline hyclate | 6.79 |
| Palatable material | Yeast extract | 15.57 |
| | Chicken flavor | 3.66 |
| Binder | Maltodextrin | 12.38 |
| | Pregelatinized starch | 10.99 |
| | Guar gum | 0.96 |
| | Xanthan gum | 0.41 |
| Humectant | Soya oil | 5.95 |
| | Glycerin | 7.79 |
| | Sorbitol | 8.89 |
| Filler | Dextrose | 7.79 |
| | Microcrystalline cellulose | 10.47 |
| Disintegrant | Croscarmellose | 4.12 |
| Lubricant | PEG 6000 | 1.83 |
| | Stearic acid | 2.00 |
| | Magnesium stearate | 0.40 |

Furthermore, the tablet produced in Example 1 has no measurable hardness. Hardness is the force required to break a tablet, (expressed in Kg). Hardness of these soft tablets according to this example cannot be measured as the tablet bends upon applying pressure.

Friability is defined as the % of weight loss by tablets due to mechanical action during a conventional tumbler test. 20 tablets were placed in a tumbler and exposed to rolling and repeated shocks as they fall 6 inches in each turn within the apparatus. After 4 minutes of this treatment (100 revolutions) the tablet were weighed and the weight compared with the initial weight. Since the weight was not changed, measured friability was.

Secability of the ½ and ¼ tablets produced according to the invention were in conformity with the pharmacopoeia 0478 2.9.5.

Example 2: Soft Tablet Composition Comprising Milbemycin and Praziquantel

In a granulator, all powder ingredients are mixed together in the amounts specified below:

| | |
|---|---|
| Milbemycin | 4 g |
| Praziquantel | 10 g |
| Malted yeast | 52.94 g |
| Chicken flavor | 10.90 g |
| Maltodextrin | 39.87 g |
| Pregelatinized starch | 43.60 g |
| Guar gum | 3.27 g |
| Xanthan gum | 1.40 g |
| Dextrose | 31.14 g |
| Microcrystalline cellulose | 18.68 g |
| Croscarmellose | 14.01 g |
| PEG 6000 | 6.23 g |

Then, humectants are sprayed onto the blend (sorbitol 30.21 g and glycerin 24.91 g premixed together) followed by the oily humectant soya oil (20.24 g). The resulting material is mixed to generate wet granules.

The wet granules are then spread on tray and left standing for 24 hours at a temperature of about 20° C.

The granules are then milled with an oscillating granulator through a 1250 μm sieve Granules were spread and left at ambient temperature for 6 hours.

The resulting granules were first blended in a blender with 20.40 g of microcrystalline cellulose, followed by addition of 6.80 g of stearic acid, and 1.36 g of magnesium stearate.

The granules were then compressed in a tablet press into tablets.

Tablets of 340 mg were produced containing 4 mg mylbemycin and 16 mg praziquantel. These tablets were oblong with a punch size of 12.7 mm.

The resulting tablet composition contains the following components:

| Ingredient | Product | WT % |
| --- | --- | --- |
| Active ingredient | Milbemycin | 1.18 |
| | Praziquantel | 2.94 |
| Palatable material | Malted yeast | 15.57 |
| | Chicken flavor | 3.21 |
| Binder | Maltodextrin | 11.74 |
| | Pregelatinized starch | 12.82 |
| | Guar gum | 0.96 |
| | Xanthan gum | 0.41 |
| Humectant | Soya oil | 5.95 |
| | Glycerin | 7.33 |
| | Sorbitol | 8.88 |
| Filler | Dextrose | 9.16 |
| | Microcrystalline cellulose | 11.50 |
| Disintegrant | Croscarmellose | 4.12 |
| Lubricant | PEG 6000 | 1.83 |
| | Stearic acid | 2.00 |
| | Magnesium stearate | 0.40 |

The invention claimed is:

1. A process for preparing a solid soft tablet composition comprising at least one active ingredient, at least one excipient, and a humectant at a concentration between 15.00% and 35.00% by weight, relative to the total weight of the solid soft tablet composition, wherein the process comprises the following steps:
   i) mixing said at least one active ingredient, said at least one excipient, and said humectant in a granulator to obtain wet granules;
   ii) spreading the wet granules and letting stand for 2 to 24 hours between 15 and 25° C.;
   iii) compressing the granules obtained after step ii) with a tablet press; and
   iv) collecting a solid soft tablet composition,
   wherein the solid soft tablet composition is not sticky, is not friable and is hard enough to be manipulated and packaged; and
   wherein the humectant is a combination of glycerin, sorbitol, and soya oil.

2. The process according to claim 1, wherein the at least one active ingredient is selected from the group consisting of anti-infectives, antibiotics and sulfonamides, cardiotonics, internal and external anti-parasitics, insecticides, insect growth inhibitors, anti-arthritics, anti-inflammatories whether or not steroidal, anti-histaminics, hormones, gastro-intestinal dressings and sedatives, anti-ulcer agents and substitution flora, anti-diarrhoeals, hepato-protectors, anti-spasmodics, laxatives, intestinal antiseptics, respiratory analeptics, antitussives, bronchodilators, bronchial and mucolytic fluidifiers and respiratory antiseptics, analgesics, sedatives and tranquilizers, anti-epileptics, anaesthetics, orexigenics, anorexigenics, interleukins and interferon, antimitotics and cytostatics, macro-, micro-nutrients and trace elements, vitamins, plant extracts, extracts from animal organs, and a mixture thereof.

3. The process according to claim 1, wherein the at least one active ingredient is an active nutraceutical ingredient or a food supplement ingredient, selected from the group consisting of plant extracts, animal extracts, substitution flora, macro-nutrients, micro-nutrients and trace-elements, and a mixture thereof.

4. The process according to claim 1, wherein the at least one excipient is selected from the group consisting of a palatable material, a binder, a lubricant, a filler, a disintegrant, and a mixture thereof.

5. The process according to claim 1, wherein said at least one excipient is a palatable material selected from the group consisting of meat, meat powders, fish powders, cheese powders, milk derivatives, liver powder, yeasts, yeast extracts, vegetable fibers, malt extract, fenugreek, apple, carrot, fodder beet, sugar beet, thyme, alfalfa, sugar cane, cereals, their flours and a mixture thereof, crystallized sugar, powder sugar glucose, invert sugar, molasses, caramel, honey and its derivatives, sodium chloride, and a mixture thereof.

6. The process according to claim 1, wherein said at least one excipient is a palatable material selected from the group consisting of a pig liver powder, a chicken liver flavor, a chicken flavor, yeast extract, malt extract, and a mixture thereof.

7. The process according to claim 1, wherein said at least one excipient is a binder selected from the group consisting of polyvinyl alcohol polymers, polyvinylpyrrolidone, the copolymers of vinylpyrrolidone and vinyl acetate, maltodextrin, carboxymethylcellulose and salts and derivatives thereof, alginic acid and its salts, zein, pectins, arabic gum, acacia gum, gum tragacanth, karaya gum, xanthan gum, guar gum, carrageenans, gelatin, pullulan polymers, agar polymers, starches and their derivatives, acrylic acid cross-linked with polyalkenyl ethers, and a mixture thereof.

8. The process according to claim 1, wherein said at least one excipient is a lubricant selected from the group consisting of polyethylene glycol, magnesium or calcium stearate, stearic acid, vegetable oil, hydrogenated glyceryl palmitostearate, sodium stearyl fumarate, and a mixture thereof.

9. The process according to claim 1, wherein said at least one excipient is a filler selected from the group consisting of maltodextrin, cyclodextrin, lactose, talc, silica, silicates, phosphates, cellulose, cellulose powder, microcrystalline cellulose, croscarmellose, mica, carbonates, sugar, and a mixture thereof.

10. The process according to claim 1, wherein said at least one excipient is a disintegrant selected from the group consisting of croscarmellose, crosspovidone, starch, sodium starch glycolate and a mixture thereof.

11. The process according to claim 1, wherein the collected solid soft tablet further comprises at least one preservative selected from the group consisting of parabens, benzoic acid, sodium benzoate, sorbic acid, potassium sorbate, and a mixture thereof, and/or at least one antioxidant selected from the group consisting of ascorbic acid, its salts and derivatives, sodium or potassium metabisulphite, sodium bisulphite, butylhydroxyanisole, butylhydroxytoluene, gallic acid and its derivatives, and a mixture thereof, and/or at least one chelating agent selected from the group consisting of EDTA and its salts, tartaric acid and its salts, and a mixture thereof.

12. The process according to claim 1, comprising the following steps:
- i) a) mixing the at least one active ingredient, the at least one palatable material, at least one binder, the at least one filler, the at least one lubricant, and the at least one disintegrant in a granulator to form a blend;
- i) b) spraying the humectant onto the blend of step i) a) and mixing to obtain wet granules;
- ii) a) spreading the wet granules obtained after step i) b) and letting stand for 2 to 24 hours between 15 and 25° C.;
- ii) b) milling the granules obtained after step ii) a) with an oscillating granulator, and then sifting through an 800 to 2000 μm sieve;
- ii) c) optionally letting the milled granules obtained after step ii) b) stand for 2 to 24 hours at room temperature;
- iii) a) optionally blending the milled granules obtained after step ii) b) or step ii) c) with at least one disintegrant and/or at least one filler in a blender;
- iii) b) blending the granules obtained after step ii) b), ii) c) or iii) a) with at least one lubricant in a blender;
- iii) c) compressing the blend obtained after step iii) b) with a tablet press; and
- iv) collecting the solid soft tablet composition.

13. The process according to claim 1, wherein the collected solid soft tablet composition comprises:
- between 0.01 and 20.00% by weight of said at least one active ingredient,
- between 15.00 and 30.00% by weight of at least one palatable material,
- between 20.00 and 40.00% by weight of at least one binder,
- between 0.10 and 10.00% by weight of at least one lubricant,
- between 10.00 and 30.00% by weight of at least one filler, and
- between 0.10 and 10.00% by weight of at least one disintegrant, relative to the total weight of the collected solid soft tablet composition.

14. The process according to claim 1, wherein said at least one excipient is a binder selected from the group consisting of maltodextrin, pregelatinized starch, xanthan gum, guar gum, and a mixture thereof.

15. The process according to claim 1, wherein said at least one excipient is a lubricant selected from the group consisting of polyethylene glycol 6000, magnesium stearate, stearic acid, and a mixture thereof.

16. The process according to claim 1, wherein said at least one excipient is a filler selected from the group consisting of cellulose, microcrystalline cellulose, lactose, sugar, and a mixture thereof.

* * * * *